(12) United States Patent
Hill et al.

(10) Patent No.: US 7,907,758 B2
(45) Date of Patent: Mar. 15, 2011

(54) METHOD AND SYSTEM FOR MAINTAINING CONSISTENT ANATOMIC VIEWS IN DISPLAYED IMAGE DATA

(75) Inventors: Steven Hill, Seattle, WA (US); Paul Detmer, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1011 days.

(21) Appl. No.: 11/576,366

(22) PCT Filed: Oct. 5, 2005

(86) PCT No.: PCT/IB2005/053266
§ 371 (c)(1),
(2), (4) Date: Mar. 30, 2007

(87) PCT Pub. No.: WO2006/038188
PCT Pub. Date: Apr. 13, 2006

(65) Prior Publication Data
US 2007/0269092 A1    Nov. 22, 2007

Related U.S. Application Data

(60) Provisional application No. 60/617,127, filed on Oct. 7, 2004.

(51) Int. Cl.
*G06K 9/00* (2006.01)
*A61B 8/00* (2006.01)
(52) U.S. Cl. .......................... 382/128; 600/443
(58) Field of Classification Search .................. 382/128, 382/129, 130, 131, 132, 133, 134; 600/407, 600/410, 425, 427, 443, 463; 128/915, 916, 128/200.16; 424/9.5
See application file for complete search history.

(56) References Cited

U.S. PATENT DOCUMENTS

| 5,538,004 A | 7/1996 | Bamber |
| 6,589,176 B2 * | 7/2003 | Jago et al. ..................... 600/443 |
| 7,576,740 B2 * | 8/2009 | Dicken ......................... 345/424 |
| 2005/0096543 A1 * | 5/2005 | Jackson et al. ................ 600/441 |

OTHER PUBLICATIONS

Kozerke, S., et al., "Heart Motion Adapted Cine Phase-Contrast Flow Measurements Through the Aortic Valve," Magnetic Resonancce in Medicine: Official Journal of the Society of Magnetic Resonance in Medicine/Soc. of Mag. Res. in Med., Nov. 1999, vol. 42, No. 5, Nov. 1999, pp. 970-978, XP02372021, ISSN: 0740-3194.

Guyon, J-P, et al., "VETOT, Volume Estimation and Tracking Over Time: Framework and Validation," Lecture Notes in Computer Science, Springer Verlag, New York, NY, US, vol. 2879, No. Part 2, 2003, pp. 142-149, XP002359024, ISSN: 0302-9743.

Schwartz, S. L., et al., "Automatic Backscatter Analysis of Regional Left Ventricular Systolic Function Using Color Kinesis," The American Journal of Cardiology, vol. 77, No. 15, Jun. 15, 1996, pp. 1345-1350, XP002372022, ISSN: 0002-9149.

* cited by examiner

*Primary Examiner* — Abolfazl Tabatabai
(74) *Attorney, Agent, or Firm* — W. Brinton Yorks, Jr.

(57) ABSTRACT

The present invention relates to an ultrasound diagnostic imaging system and method, wherein volumentric data in respect of an anatomical region of interest is acquired throughout a physiological cycle in relation thereto, a 3D view of the volumetric data is built, the motion of a structure of interest (in space and/or time) is analysed within the volume throughout the above-mentioned physiological cycle, and this motion is used to move a 3D view of the structure of interest, as presented to a user, so that it tracks the structure of interest and retains it centred in the 3D view.

6 Claims, 4 Drawing Sheets

METHOD AND SYSTEM FOR MAINTAINING CONSISTENT ANATOMIC VIEWS IN DISPLAYED IMAGE DATA

CROSS REFERENCE TO RELATED APPLICATION

This application claims the benefit of U.S. provisional application Ser. No. 60/617,127 filed Oct. 7, 2004, which is incorporated herein.

FIELD OF THE INVENTION

This invention relates to a method and system for maintaining consistent anatomic views in displayed image data, and finds particular application in the field of processing medical images, such as ultrasound images, with respect to an anatomical region of interest.

BACKGROUND OF THE INVENTION

One of the advantages that certain medical imaging techniques, such as diagnostic ultrasound imaging, has over many other diagnostic imaging modalities is the ability to produce realtime images. This advantage has been especially significant in echocardiography where the physiology of a continually moving organ, i.e. the heart, is the subject of study. Realtime imaging has been a virtual necessity in echocardiography, as compared with abdominal and obstetrical applications where the tissues and organs being studied are stationary and may be readily examined by static imaging.

A wide range of cardiac studies can be performed using recorded, realtime moving images, and qualitative review of such images by trained medical personnel can detect congenital heart defects, large aneurysms or stenoses in the major coronary arteries, and other gross anatomical abnormalities. Analyses such as heart pumping capacity measurements, wall motion abnormalities blood perfusion studies in the myocardium and coronary vessel tracking provide complementary quantitive diagnostic information.

One major problem in evaluating, for example, cardiac structures from two- and three-dimensional data has been to ensure that one is observing the same tissue or structure as the heart moves through the cardiac cycle. What is desired is a consistent view of the tissue structure throughout the cardiac cycle, even though the structure is moving along with the rest of the heart. For example, when observing the mitral valve annulus, left ventricular outflow tract or a short-axis view of the left ventricle at a particular level, a plane defining an MPR slice or oriented 3D view of the structure is currently defined using the frame of reference of the image acquisition. However, because the structure of interest is moving relative to the imaging frame of reference, along with the rest of the tissue, it may pass into and out of the view, which has the effect of complicating the process of evaluating the structure. This is one reason why it took many years to appreciate the saddle shape of the mitral annulus, for example.

SUMMARY OF THE INVENTION

It is an object of the present invention to provide a system and method for displaying image data of an anatomical region of a subject so as to facilitate visualisation of a given structure (e.g. a cardiac structure) therein, which may be moving and/or may follow a tortuous path through at least a portion of the region, from two- or three-dimensional data throughout a physiological cycle, such as the cardiac cycle.

In accordance with the present invention, there is provided a system for displaying image data acquired from a region, said region including therein at least one structure which is subject to movement, the system comprising means for identifying a portion of said moving structure, tracking movement of said identified portion corresponding to movement of said moving structure, and compensating for said movement to provide a stable displayed view of said region throughout said movement thereof.

Also in accordance with the present invention, there is provided a method for displaying image data acquired from a region, said region including therein at least one structure which is subject to movement, the method comprising identifying a portion of said moving structure, tracking movement of said identified portion corresponding to movement of said moving structure, and compensating for said movement to provide a stable displayed view of said region throughout said movement thereof.

The system defined above is intended to encompass the use of such a system in an off-line workstation environment. However, the present invention also extends to an imaging system including means for acquiring or receiving image data, a screen for displaying said image data, and a system as defined above.

Thus, in accordance with the invention, the portion of the moving structure which is of interest for evaluation and/or diagnostic purposes can be retained within the viewed image of the respective region, thereby improving the visualisation and relationship of structures, such as cardiac structures, from two- or three-dimensional image data throughout a physiological (e.g. cardiac) cycle so as to facilitate and simplify the evaluation/diagnostic process.

The present invention finds particular application in medical imaging systems, such as ultrasound imaging systems, for the purpose of evaluating anatomical regions of interest, such as cardiac structures, from two- or three-dimensional image data acquired in respect of the region of interest. Such image data may be live or previously captured.

The above-mentioned structure may be subject to movement as a result of each physiological cycle in a sequence of such cycles, in which case the tracking means may be arranged to track movement of said structure throughout one or more of said physiological cycles. The system may comprise means for re-positioning the identified portion of the structure within a displayed image so as to compensate for the movement and retain the identified portion within the displayed view.

In a preferred embodiment, the system includes means for acquiring volumetric image data with respect to an anatomical region of interest throughout a physiological cycle. Then either a two-dimensional tomographic slice image or a rendered three-dimensional view from a particular viewpoint of said anatomical region of interest can be assembled from the volumetric data. Thus, the process of tracking movement of a structure within the anatomical region of interest is achieved by analysing motion of the structure of interest within the volume data throughout the physiological cycle. That motion can then be compensated for as part of assembling the two-dimensional tomographic slice or rendered three-dimensional view throughout the physiological cycle.

These and other aspects of the invention will be apparent from and will be elucidated with reference to the embodiments described hereinafter.

BRIEF DESCRIPTION OF THE DRAWINGS

The present invention will now be described in more detail, by way of example, with reference to the accompanying drawings, wherein.

DETAILED DESCRIPTION OF THE INVENTION

The following specific description refers to a system and method of displaying image data in respect of the cardiac region. However, it will be appreciated that the present invention may also find application in medical imaging of other anatomical region of interest including dynamically moving organs or structures that follow a non-uniform path therethrough.

In the first instance, volumetric data in respect of the cardiac region of a subject is acquired throughout the respective cardiac cycle. It will be appreciated that many different techniques for acquiring such volumetric data will be known to a person skilled in the art and the present invention is not intended to be limited in this regard. One suitable method of acquiring the desired volumetric data is known as ultrasound diagnostic imaging.

Figure 1:
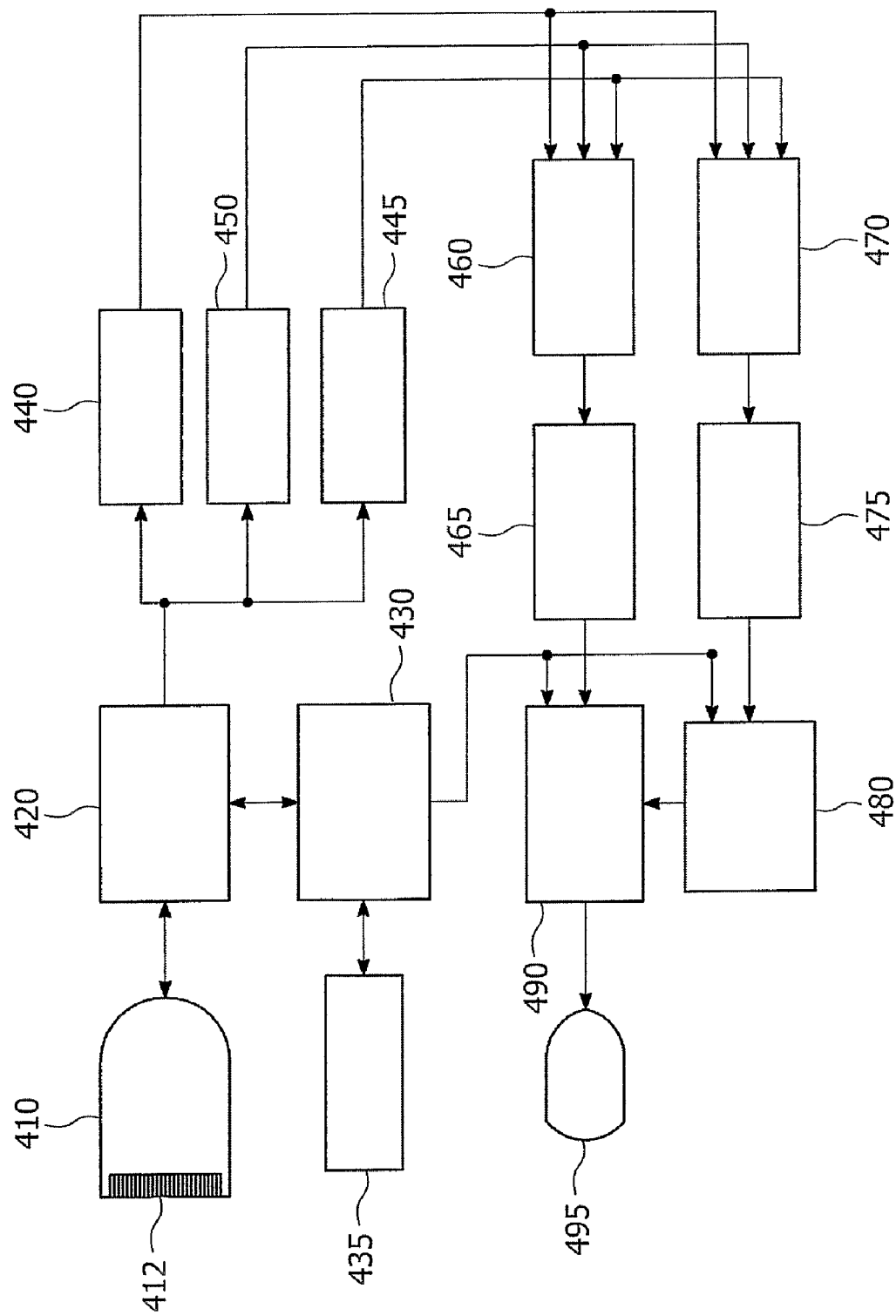
FIG. 1 is a schematic block diagram illustrating a typical configuration of an ultrasound imaging system according to an exemplary embodiment of the present invention.

Referring to FIG. 1 of the drawings, there is illustrated schematically an ultrasound system for acquiring real-time cardiac images, either as 2D tomographic slices or as volumetric image data. A probe or scanhead 410 which includes a 1D or 2D array transducer 412 transmits ultrasonic waves and receives ultrasonic echo signals. This transmission and reception is performed under control of a beamformer 420 which possesses received echo signals to form coherent beams or raw echo signals from the anatomy being scanned. The echo information from the beamformer is then processed by the B-mode processor, 450, the Doppler processor, 440, and, if contrast agents are used during imaging, the contrast signal processor, 445. The B-mode processor performs functions that include, but are not limited to, filtering, frequency and spatial compounding, harmonic data processing and other B-Mode functions well known in the art. The Doppler processor applies conventional Doppler processing to the echoes to produce velocity and Doppler power signals. The contrast processor applies specific processing to echo signals that are obtained when contrast agents are present in the tissue being scanned. The processed data is then passed through either a 2D scan converter 460 or a 3D scan converter 470, depending on whether a 2D tomographic or 3D volumetric region of tissue is being imaged. The scan converter geometrically corrects the data from the linear or polar geometry that the scanhead acquired the beams in, to a Cartesian format (x,y or x,y,z) with appropriate scaling in each dimension. Each scan converted image or 3D volume is then placed in a 2D cineloop memory, 465, or 3D volume memory, 475. The cineloop memory blocks store a few seconds up to several minutes worth of recent 2D or 3D data, depending on the type of data being acquired. The Volume MPR slice display processor and 3D renderer, 480, processes volume data from the 3D volume memory based on the central controller, 430, and user input from the user interface, 435, to provide one or several 2D MPR slice images and/or a volume rendered image of the 3D volume from a given viewpoint using methods well known in the art. The display processor, 490, based on input from the central controller, 430, takes 2D images either from the 2D cineloop memory or the volume MPR slice view processor and 3D rendered, adds graphics overlays and text annotation (e.g. patient information) and passes the composted images on to the display, 495, for presentation to the operator. The central controller can direct the display processor to display the most recently acquired data in memory as a real-time display, or it can replay sequences of older 2D or 3D volume data.

Thus, a two-dimensional tomographic slice view or a rendered three-dimensional view of the acquired volumetric data from a particular viewpoint is built and displayed, using techniques specific to the method of acquiring the data, which will be well known to a person skilled in the art.

Next, consider the case where a selected region or structure of interest is moving, along with the rest of the tissue of a dynamically moving organ such as the heart. In prior art arrangements, the structure of interest may move in and out of the displayed view, thereby complicating the evaluation of the structure by the medically skilled user, as illustrated for a cardiac imaging example in FIG. 2 of the drawings, which shows an ultrasound planar view and associated M-Mode display at two points on the cardiac cycle. The image sector representing a side planar view of the volume at one point in the cardiac cycle, 500, shows the heart chamber wall, 510, and an associated structure on the wall such as a valve structure, 530. An M-Mode line, 505, passes through both structures. A graphic line shows the location of an alternate imaging plane, 540, passing through both structures. This plane, whose image is not shown, would display an image of the structures from the top of the heart at a particular angle. Below side plane 500 is the associated M-Mode display line, 507, showing one-dimensional peaks of the chamber wall, 515, and the valve structure, 535, as well as the location of the alternate plane, 540, relative to these structures along the M-Mode line.

Figure 2:
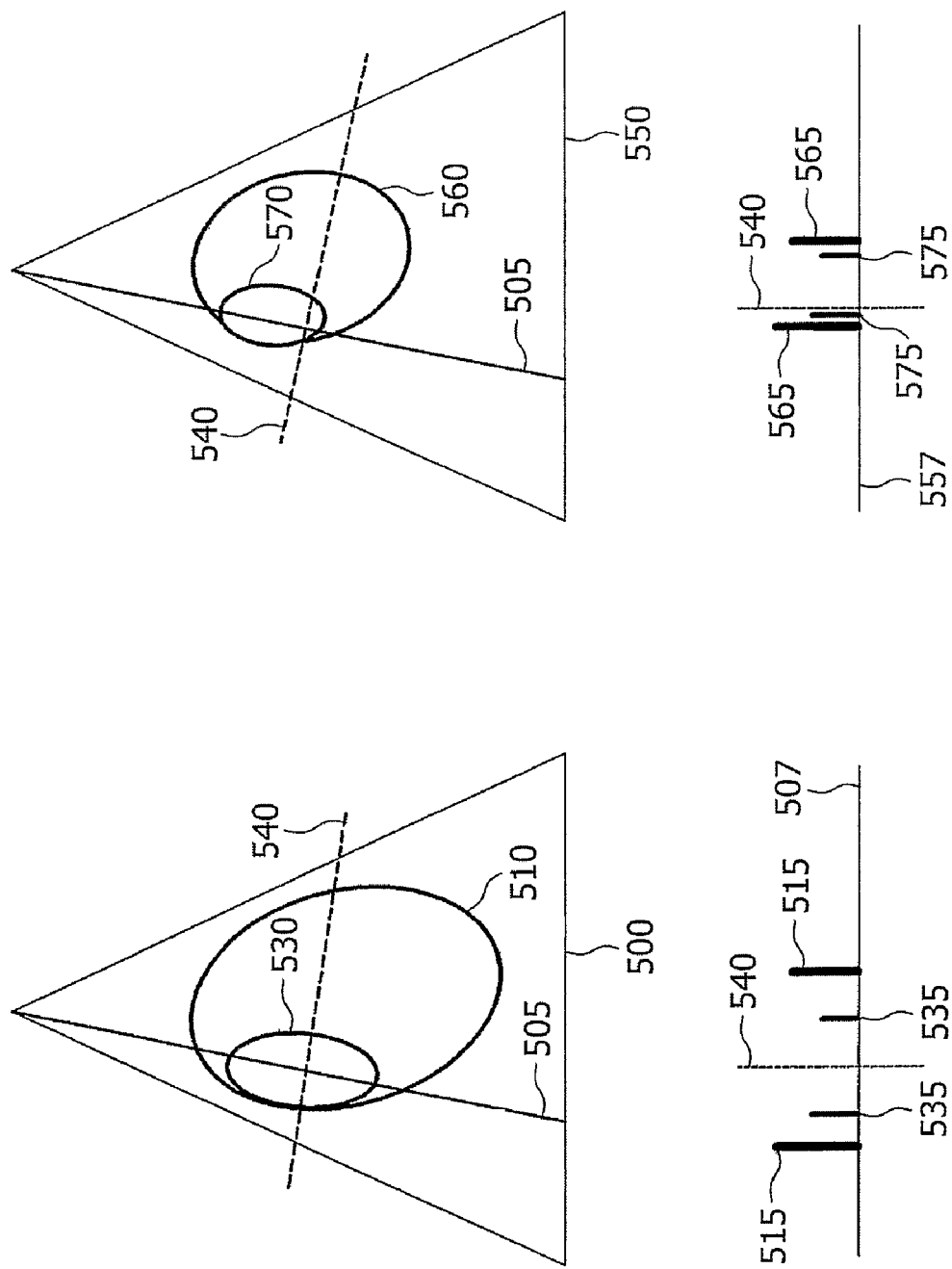
FIG. 2 is a schematic diagram illustrating how a feature moves in and out of a fixed viewing plane during live volume imaging.

The right-hand side of FIG. 2 shows the same side planar view of the volume, 550, at a later point in the cardiac cycle, revealing a smaller heart chamber, 560, and a smaller, shifted valve structure, 570. Also shown are M-Mode line, 505, and alternate imaging plane, 540, in the same position in the image side plane. Below this later side plane, 550, is the accompanying M-Mode display, 557, showing the new locations of the chamber wall peaks, 565, valve structures, 575, and the shifted location of the alternate plane, 540, relative to the cardiac structures. Note that at this later point in the cardiac cycle, the alternate plane, 540, now cuts through the valve structure at a different level, possibly leading to confusion about its actual size and function.

In order to alleviate this problem, the present invention includes means for analysing motion of the structure of interest within the volume throughout a physiological (i.e. cardiac) cycle, and means for compensating for this motion, throughout the cardiac cycle, in the three-dimensional view provided to the user. The aim of the present invention is to move the displayed view provided to the user so that it "tracks" movement of the structure of interest (or, for example, the tortuous path followed by a structure of interest within the anatomical region of interest), and thereby to keep the structure of interest, preferably but not necessarily centrally, within the view.

In other words, as the volumetric data is acquired or retrospectively replayed from memory, a motion analysis technique may be used to determine the motion path of the structure of interest within the volume, and this motion may be used to move the view presented to a user so that it tracks the structure.

This tracking capability could also be tied to a trim plane or sculpting surface that are often used to remove image data that overlies features of interest. When performing 3D imaging, the operator often most remove image data that obscures underlying features in the volume. The tools provided to do this range from simple trim planes to complex surface sculpting tools that permit overlying tissue to be "cut" away as a surgeon or sculptor will do. Often this plane or surface lies very close to the feature of interest and will move along with the feature. In the feature tracking capability is tied to the plane or surface, then the trimming capability will follow the feature along with the viewing plane, again providing a clear view of the moving feature as it moves.

There are many known techniques for analysing the motion of the structure of interest which could be employed in the present invention, as will be apparent to a person skilled in the art. A selected few of these techniques will now be briefly described, but it will be appreciated that other techniques may be employed, and the present invention is not intended to be limited in this regard.

For example, the motion analysis may be based on a simple 2D motion of a feature along a straight line through a key structure (i.e. the structure of interest) to identify a motion vector along the line. M-Mode echocardiography is a well-known technique which has, in the past, been found to be particularly useful in assessment of left ventricular wall mass, left arterial and left ventricular chamber dimensions, and motion over short time periods. In M-Mode (motion mode) imaging, ultrasound echoes (in the case of an ultrasound imaging system) are repeatedly taken acquired along a pre-selected M-line emanating from the transducer. The strength of the echoes are mapped as brightness on successive acquisitions of the M-line are consecutively and adjacently displayed, so that the structure moving through the relevant M-line is reproduced in motion.

Figure 3:
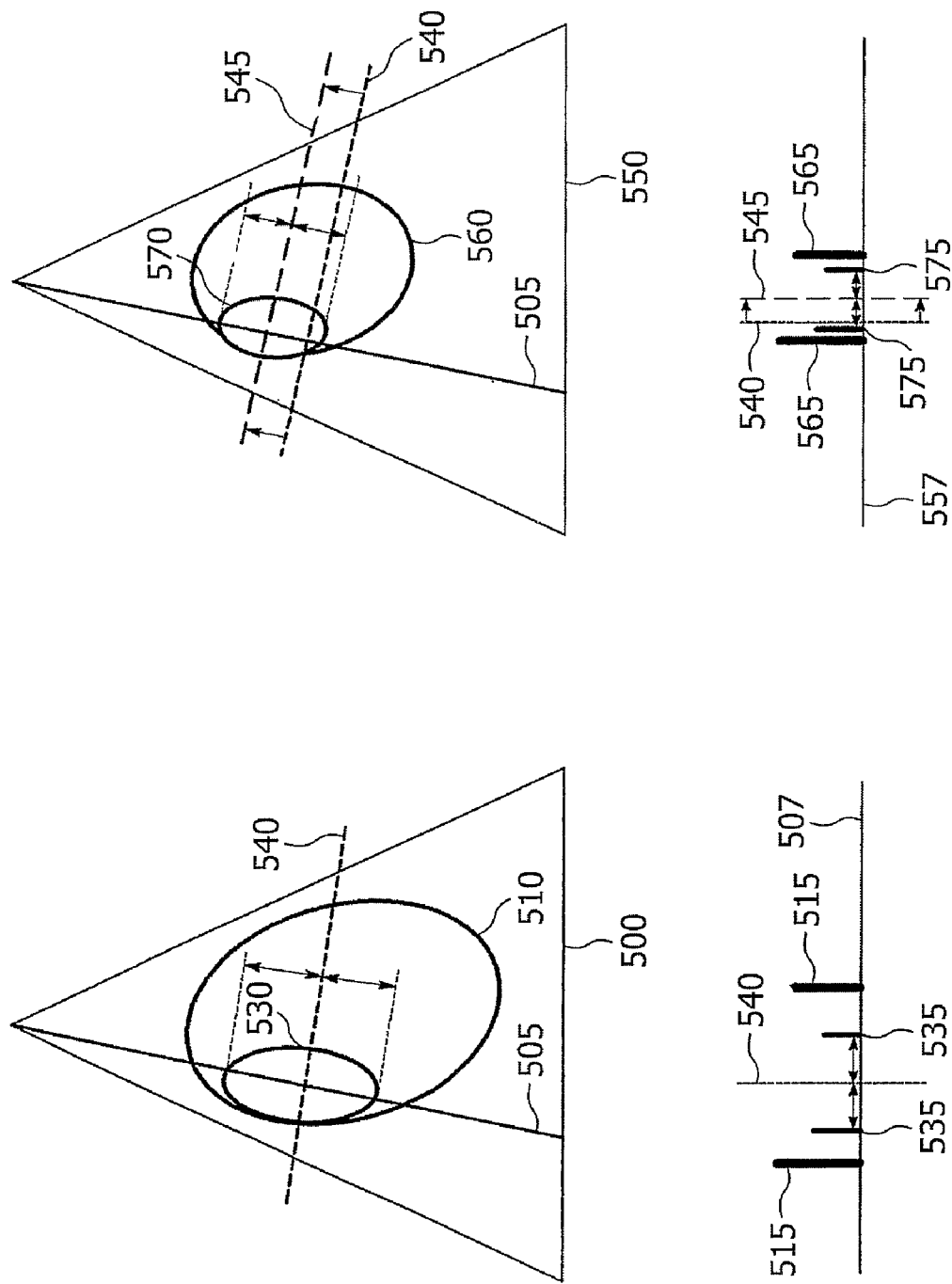
FIG. 3 is a schematic diagram illustrating how identifying a selected anatomic feature compensates and typing the viewing plane to the moving feature allows the display of an image plane or viewpoint to track the feature, giving a consistent view of the feature.

In an exemplary embodiment of the present invention, the 3D view or slice plane would be tied to a bright, dark or patterned feature in the M-line and tracking to the feature would be performed with the plane oriented perpendicular along the M-line in the volume. FIG. 3 illustrates this using the imaging situation described earlier with reference to FIG. 2. In this case, the alternate imaging plane, 540, is identified in the M-Mode display, 507, as being halfway between the valve structure peaks, 535. This forces the alternate plane, 540, to pass through the centre of the valve structure, 530, at the beginning of the cardiac cycle. As the cardiac cycle progresses, the peaks of the valve structure, 575, and cardiac chamber walls, 565, have moved in the M-Mode display, 557, as shown previously. By keeping the alternate imaging plane's location halfway between the valve structure peaks, at 545, the plane is kept centred on the valve structure and follows the anatomy of interest, rather than remaining fixed to the other image plane, 550, at location 540. This allows the alternate plane to move between locations 540 and 545 as the anatomy moves, providing a clearer view of the valve structure and function.

Note that the M-Line would not need to emanate directly from the transducer, but could be any straight line or curved path through the acquired volume. The use of M-lines in 2D and 3D models is known, and is described in more detail in, for example, International patent application No. WO2004/072903.

The concept of tracking patterns of features can easily be seen to be extended to 2D features or even 3D features. In this case, 2D or 3D models or matching images of features could be selected from recently acquired data sets or a library of features and applied to selected regions of the volume data. Using methods such as matched filtering, mathematical morphology or other methods well known in the art, the feature locations could be tracked through the volume data and the MPR slice or 3D rendered view planes tied to a fixed or user selected orientation relative to the feature as it moved. Using this method, feature characteristics that changed in time through the cycle could be matched adaptively. The viewpoint could even be set up to change as the characteristics of the feature changed. For example, if the aortic valve was being monitored, as the valve opened and closed, the orientation of the view could be changed to lie parallel to one of the leaflet planes. This would mean tracking the valve opening in 2D or 3D as the valve opened and closed using a model of an ideal valve or a sequence of images or previously acquired 3D data.

Another method of motion analysis may be based on the use of acoustic quantification (AQ) or colour kinesis to identify more complex motion in 2D slices.

Colour kinesis (CK) is a known echocardiographic method that displays endocardial motion as colour layers on a single end-systolic frame (see, for example, Schwartz S. L., Cao Q., Vannan M. A. et al: "Autanatic Backscatter Analysis of Regional Left Ventricular Systolic Function using Color Kinesis", Am. J. Cardiol. 1996, 77, 1345-1350; Lang R. M., Vignon P., Weinert L. et al: "Echocardiographic Quantification of Regional Left Ventricular Wall Motion with Color Kinesis", Circulation 1996, 93, 1877-1995; Mor-Avi V., Goday I. E., Lang R. M: "Color Kinesis New Technique or just another Display of Acoustic Qualification?", Echocardiography 1999, 16, 95-103). The method is an extension of semi-automatic edge detection technology (i.e. acoustic quantification) that permits continuous on-line quantification of the dimensions of each cardiac chamber by differentiating the acoustic backscatter characteristics of blood from that of myocardium (see, for example, Vered Z., Barzilai B., Mohr G. A., et al "Quantitative Ultrasonic Tissue Characterization with Realtime Integrated Backscatter Imaging in Normal Human Subjects and in Patients with Dilated Cardiomyopathy"., Circulation 1987, 76, 1067-1073).

The tracking capability could also be tied to a trim plane or sculpting surface that are often used to remove image data that overlies features of interest. When performing 3D imaging, the operator often most remove image data that obscures underlying features in the volume. The tools provided to do this range from simple trim planes to complex surface sculpting tools that permit overlying tissue to be "cut" away as a surgeon or sculptor will do. Often this plane or surface lies very close to the feature of interest and will move along with the feature. If the feature tracking capability is tied to the plane or surface, then the trimming capability will follow the feature along with the viewing plane, again providing a clear view of the moving feature as it moves.

Figure 4:
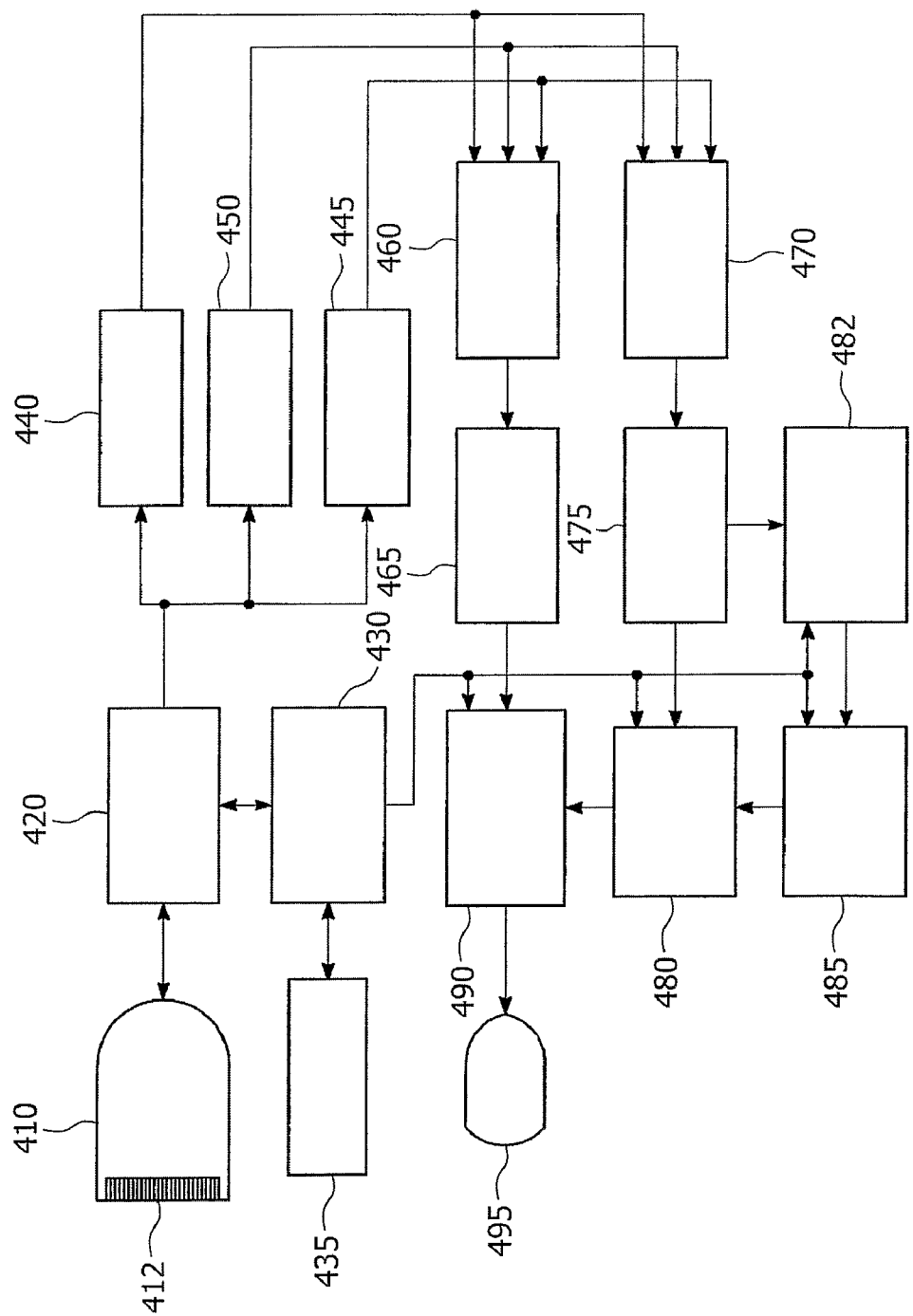
FIG. 4 is a schematic block diagram illustrating one possible exemplary method to implement the tracking of anatomic features to display a consistent view.

Thus, any one of the above (or other) motion analysis techniques may be used to determine the motion path of the structure of interest within the volume and use this motion to move the 3D view presented to a user so that the structure is tracked. FIG. 4 illustrates how one might add the functionality to the ultrasound system described earlier in FIG. 1. The anatomic feature detector, 482, would analyze the most recently acquired volume and determine the location and orientation of the feature of interest. Using this information, the 3D display motion tracking function, 485, would use this information and possibly information from previous volumes, to update the location and orientation of the MPR slice views and/or 3D rendered viewpoints. The updated viewpoint locations would then be passed to the slice view processor and 3D renderer to provide the updated view for eventual display. It will be appreciated that many different techniques will be known to a person skilled in the art and the present invention is not intended to be limited in this regard.

Note that the 3D view need not be planar, it is envisaged for example, that a volume loop could be acquired, a series of slice views obtained, and key structures in the volume data at key points identified through the cardiac cycle. Then interpolation techniques could be used to draw complex surfaces through the key points, and the surfaces could be displayed as 2D images. Additionally, simple 2D planes or complex surfaces could also be made to follow complex paths (i.e. such, complex paths could be tracked) in space, as well as time. For example, a short axis view of a vessel could follow a path along the vessel, determined from the vessel's wall features, so that the view plane shows the diameter of the vessel regardless of the tortuous path of the vessel.

As a result of the exemplary embodiment of the present invention as described above, the structure of interest is kept centred in the 3D view. Analysis of the data and diagnostic are facilitated. The present invention is considered to be particularly relevant to ultrasound diagnostic imaging systems and techniques, most preferably, but exclusively cardiac applications thereof.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for displaying ultrasound image data of an anatomical region of a subject, said region having a first movement and including therein at least one structure of interest, which is subject to a second movement, the system comprising means for providing data of said anatomical region, characterized in that it further comprises:

means for determining, from said data, the location of two peaks, along an M-line of an M-Mode display having a predetermined direction passing trough said structure of interest, said peaks corresponding respectively to an intersection position between said structure and said M-line at a first moment, means for setting the location of a plane in such a way that it crosses the structure of interest and said M-line in a predetermined direction and at a predetermined distance between said peaks, means for moving said plane at a second moment, so that said distance is kept constant if the peaks have moved with respect to the first moment, and means for continuously displaying the structure within the anatomical region from a viewpoint depending on the location of the plane, so that the second movement of the displayed structure is stabilized.

2. A system according to claim 1, wherein the data are provided in a stream and the displayed image is stabilized on the fly.

3. A system according to claim 2, wherein the data are 2D data or 3D data.

4. A system according to claim 1, wherein the direction of the plane is normal to the M-Line.

5. A system according to claim 1, wherein the anatomical region and the structure corresponds to the heart and the valve annulus, respectively.

6. A method for displaying ultrasound image data of an anatomical region of a subject having a first movement, said region including therein at least one structure of interest, which is subject to a second movement, characterized in that it comprises the following steps:

providing data of said anatomical region, determining, from said data, the location of two peaks, along an M-line of an M-Mode display having a predetermined direction passing trough said structure of interest, said peaks corresponding respectively to an intersection position between said structure and said M-line at a first moment, setting the location of a plane in such a way that it crosses the structure of interest and said M-line in a predetermined direction and at a predetermined distance between said peaks, moving said plane at a second moment, so that said distance is kept constant if the peaks have moved with respect to the first moment, and continuously displaying the structure within the anatomical region from a viewpoint depending on the location of the plane, so that the second movement of the displayed structure is stabilized.

* * * * *